United States Patent
Malone et al.

(10) Patent No.: US 10,123,736 B2
(45) Date of Patent: Nov. 13, 2018

(54) METHOD AND APPARATUS FOR MONITORING COMPLIANCE WITH PHYSICAL THERAPY REGIMES

(71) Applicant: XERAS MEDICAL TECHNOLOGIES, INC., Boerne, TX (US)

(72) Inventors: Mark S. Malone, Boerne, TX (US); Cory R. A. Hallam, San Antonio, TX (US)

(73) Assignee: Xeras Medical Technologies, Inc., Boerne, TX (US)

( * ) Notice: Subject to any disclaimer, the term of this patent is extended or adjusted under 35 U.S.C. 154(b) by 0 days.

(21) Appl. No.: 15/470,497

(22) Filed: Mar. 27, 2017

(65) Prior Publication Data

US 2018/0271436 A1   Sep. 27, 2018

(51) Int. Cl.

| | | |
|---|---|---|
| *A61H 1/00* | (2006.01) | |
| *A61H 1/02* | (2006.01) | |
| *A61H 5/00* | (2006.01) | |
| *A61B 5/00* | (2006.01) | |
| *A63B 21/00* | (2006.01) | |
| *A63B 23/04* | (2006.01) | |

(52) U.S. Cl.
CPC ........ *A61B 5/4833* (2013.01); *A63B 21/4039* (2015.10); *A63B 23/0494* (2013.01); *A63B 2220/833* (2013.01); *A63B 2225/093* (2013.01)

(58) Field of Classification Search
CPC ........ A61H 2201/164; A63B 2023/006; A63B 2225/093; A63B 2220/833; A61B 5/4833
See application file for complete search history.

(56) References Cited

U.S. PATENT DOCUMENTS

| 2,695,800 | A | * | 11/1954 | Soucy | A63C 11/221 248/188.4 |
|---|---|---|---|---|---|
| 2,819,873 | A | * | 1/1958 | Pearne | B66F 3/24 16/44 |
| 3,060,926 | A | * | 10/1962 | May | A61G 13/009 601/35 |
| 3,203,657 | A | * | 8/1965 | Thompson | A47C 3/24 248/171 |
| 3,415,490 | A | * | 12/1968 | Steele | B60S 9/08 254/100 |
| 3,602,492 | A | * | 8/1971 | Petrie | B25H 1/00 248/55 |
| 3,717,144 | A | * | 2/1973 | Bimler | A63B 23/0417 602/16 |

(Continued)

FOREIGN PATENT DOCUMENTS

| CN | 2885222 | 4/2007 |
|---|---|---|
| WO | WO2016157217 | 10/2016 |
| WO | WO2016195680 | 12/2016 |

OTHER PUBLICATIONS

Google Patents English translation of Foreign Patent Document 1, CN2885222, translated Jun. 26, 2017 (1 page).

(Continued)

*Primary Examiner* — Garrett Atkinson
(74) *Attorney, Agent, or Firm* — Pizarro Allen PC

(57) ABSTRACT

A system for monitoring use of knee joint flexibility rehabilitation apparatus comprises a knee joint flexibility rehabilitation apparatus, a sensor and a monitor configured to receive and display a signal from the sensor.

20 Claims, 17 Drawing Sheets

(56) References Cited

U.S. PATENT DOCUMENTS

| | | | | |
|---|---|---|---|---|
| 4,492,354 A * | 1/1985 | Rice | F16M 11/046 | 182/182.1 |
| 4,700,373 A * | 10/1987 | Miller | A61B 6/0421 | 378/177 |
| 4,844,454 A * | 7/1989 | Rogers | A61H 1/024 | 482/131 |
| 5,025,802 A * | 6/1991 | Laico | A61G 13/12 | 128/875 |
| 5,074,549 A * | 12/1991 | Harvey | A63B 23/0494 | 482/105 |
| 5,190,513 A * | 3/1993 | Habing | A63B 23/0211 | 482/140 |
| 5,333,604 A * | 8/1994 | Green | A61H 1/0255 | 601/33 |
| 5,334,028 A * | 8/1994 | Melligan | A63B 69/3608 | 434/252 |
| 5,421,115 A * | 6/1995 | McKay | F41A 23/12 | 248/163.1 |
| 5,435,411 A * | 7/1995 | Borgatti | B23D 47/025 | 144/287 |
| 5,509,894 A * | 4/1996 | Mason | A61H 1/0255 | 601/34 |
| 5,554,088 A * | 9/1996 | Zlojutro | A63B 69/004 | 482/83 |
| 5,669,863 A | 9/1997 | Ho | | |
| 5,722,627 A * | 3/1998 | Hoshino | A47C 3/24 | 248/188.4 |
| 5,746,688 A * | 5/1998 | Prager | A63B 23/03533 | 482/130 |
| 5,871,457 A * | 2/1999 | Swedberg | A47C 20/021 | 128/845 |
| 5,873,312 A * | 2/1999 | Mauro-Vetter | B25H 1/00 | 108/147.21 |
| 5,878,453 A * | 3/1999 | Stokes | A47C 20/021 | 5/630 |
| 5,935,050 A * | 8/1999 | Shahan | A63B 23/0211 | 482/140 |
| 5,957,869 A * | 9/1999 | Caruso | A61B 5/103 | 600/592 |
| 5,971,902 A * | 10/1999 | Robertson | A61H 1/0218 | 482/142 |
| 6,001,051 A * | 12/1999 | Chuan-Pin | A63B 21/0552 | 482/131 |
| 6,030,352 A * | 2/2000 | Paik | A61H 1/0237 | 482/904 |
| 6,048,293 A * | 4/2000 | Lee | A63B 23/0211 | 482/140 |
| 6,095,319 A * | 8/2000 | Noniewicz | B23D 47/025 | 198/632 |
| D432,246 S * | 10/2000 | Pestone | D25/67 | |
| 6,165,112 A * | 12/2000 | Morris | A63B 21/0552 | 482/129 |
| 6,238,320 B1 * | 5/2001 | Flanagan | A63B 3/00 | 482/130 |
| 6,254,517 B1 * | 7/2001 | Kennedy | A63B 21/04 | 482/121 |
| 6,287,244 B1 * | 9/2001 | Boos | A63B 21/068 | 482/142 |
| 6,309,330 B1 * | 10/2001 | Thornton | A63B 21/00047 | 482/140 |
| 6,371,894 B1 * | 4/2002 | Hill | A63B 21/00047 | 128/845 |
| 6,569,064 B1 * | 5/2003 | Loane | A63B 21/154 | 482/146 |
| 6,991,591 B1 * | 1/2006 | Tsatsouline | A63B 23/0211 | 482/140 |
| 7,662,077 B1 | 2/2010 | Liu | | |
| 7,695,416 B2 * | 4/2010 | Weiner | A61H 1/024 | 482/112 |
| 7,784,749 B2 * | 8/2010 | Radermacher | B65G 21/2072 | 144/287 |
| 8,012,047 B2 * | 9/2011 | Gamboa | A63B 69/00 | 473/438 |
| D666,014 S * | 8/2012 | Gruszynski | D6/353 | |
| 8,425,343 B1 * | 4/2013 | Olmos | A63B 69/0057 | 473/257 |
| 8,646,731 B2 * | 2/2014 | Burles | F16L 3/16 | 144/287 |
| 9,498,399 B1 * | 11/2016 | Juntunen | A61H 1/024 | |
| 2003/0130097 A1 * | 7/2003 | Harrison | A63B 21/0552 | 482/122 |
| 2003/0224880 A1 * | 12/2003 | Hansberry | A63B 69/0002 | 473/430 |
| 2004/0049135 A1 * | 3/2004 | Callanan | A61H 1/024 | 601/33 |
| 2005/0012000 A1 * | 1/2005 | Jones | B23Q 3/186 | 248/178.1 |
| 2006/0009336 A1 * | 1/2006 | Millet | A63B 21/00047 | 482/148 |
| 2006/0014614 A1 | 1/2006 | Szabo et al. | | |
| 2006/0217249 A1 * | 9/2006 | Webber | A63B 23/02 | 482/142 |
| 2007/0298883 A1 * | 12/2007 | Feldman | A63B 21/0023 | 463/36 |
| 2008/0058173 A1 * | 3/2008 | Mattox | A63B 21/0004 | 482/92 |
| 2008/0125959 A1 | 5/2008 | Doherty | | |
| 2008/0182730 A1 * | 7/2008 | Conley | A61H 1/0244 | 482/95 |
| 2009/0163837 A1 * | 6/2009 | Sanger | A61H 1/024 | 601/5 |
| 2009/0275447 A1 * | 11/2009 | Fishman | A63B 21/072 | 482/139 |
| 2010/0234192 A1 * | 9/2010 | Oller, Jr. | A63B 21/00047 | 482/131 |
| 2010/0256537 A1 | 10/2010 | Menga | | |
| 2011/0231995 A1 * | 9/2011 | Sedillo | A61B 6/0421 | 5/601 |
| 2012/0115693 A1 * | 5/2012 | Franques Garcia | A63B 23/0211 | 482/140 |
| 2013/0029814 A1 * | 1/2013 | D'Alessandro | A63B 22/18 | 482/139 |
| 2013/0110013 A1 * | 5/2013 | Carlson | A61H 1/024 | 601/5 |
| 2013/0197403 A1 * | 8/2013 | Sevy | A63B 21/0442 | 601/5 |
| 2013/0211291 A1 | 8/2013 | Tran | | |
| 2013/0211297 A1 * | 8/2013 | Method | A61H 1/024 | 601/34 |
| 2013/0289448 A1 | 10/2013 | Landry et al. | | |
| 2014/0051556 A1 | 2/2014 | Abassian | | |
| 2014/0066271 A1 * | 3/2014 | Gray | A63B 21/023 | 482/131 |
| 2014/0073998 A1 * | 3/2014 | Keiser | A63B 21/00185 | 601/34 |
| 2014/0087929 A1 * | 3/2014 | Sussman | A63B 21/1465 | 482/139 |
| 2014/0094721 A1 * | 4/2014 | Diallo | A61H 1/024 | 601/5 |
| 2014/0228186 A1 * | 8/2014 | Montgomery | A63B 23/0494 | 482/139 |
| 2016/0279011 A1 * | 9/2016 | Lutz | A61H 1/024 | |
| 2016/0367427 A1 | 12/2016 | Malone | | |

OTHER PUBLICATIONS

"Getting Back Out There," Trainer Rx, http://www.trainer-rx.com, Jun. 20, 2017 (7 pages).

International Search Report and Written Opinion issued in International Patent Application No. PCT/US2015/034019 dated Sep. 8, 2015 (9 pages).

International Search Report and Written Opinion issued in International Patent Application No. PCT/US2015/019336 dated Jun. 9, 2015 (6 pages).

(56) References Cited

OTHER PUBLICATIONS

International Search Report and Written Opinion in PCT2018/024651 dated Jul. 10, 2018 (15 Pages).

* cited by examiner

METHOD AND APPARATUS FOR MONITORING COMPLIANCE WITH PHYSICAL THERAPY REGIMES

FIELD

The disclosed methods and apparatuses generally relate to electronically detecting, monitoring and reporting physical therapy activity.

BACKGROUND

The efficacy of a physical therapy regime cannot be accurately gauged without knowledge of a patient's compliance with the assigned regime. Knowledge of various aspects of patient compliance is necessary for accurate assessment of the therapeutic impact of the physical therapy regime. Such aspects may generally include such matters as efficacy of the individual components of the regime, the overall efficacy of the regime, and patient feedback.

Currently, information as to regime compliance is limited to direct observation by a therapy provider and self-reporting by the patient. Because therapy providers and other healthcare professionals are often responsible for multiple patient's concurrently, direct observation is often not feasible for the entirety of an assigned regime. Self-reporting is often unreliable due to patient forgetfulness, or the natural desire for a patient to not admit non-compliance. The unreliability of self-reporting remains a major impediment to the development of effective physical therapy regimes.

Thus, there remains a need for a need for an apparatus to monitor a patient's compliance with a physical therapy regime.

DETAILED DESCRIPTION

An apparatus for monitoring patient compliance during a physical therapy regime may rely on sensors located on a physical therapy device, the peripheral components of the physical therapy device, or on both. Said sensors may indicate that the patient is actively engaged with the physical therapy device in question. Data from said sensors may be transmitted to a further device, such as a computer or data acquisition module, to process and record the output of the sensors. After processing, the sensor data may be further transmitted to an internal server and then to the cloud, or directly to the cloud, for archiving and further access by any approved entity that may require access to such records. Such approved entities may include members of the physical therapy staff, physicians, insurance representatives, researchers, and others related to the patient's care and development of physical therapy regimes.

Sensor data may also be transmitted to terminals and smart devices for use in monitoring compliance with the assigned regime. These terminals and smart devices may be accessed by a physical therapy staff member, the patient, or both. Said data may be sent in real time such that any non-compliance may be identified and acted upon during the session in question. This may allow the therapist or the patient to immediately bring the therapy being performed into compliance during the session and thus improve outcomes for the session. A patient, therapist, or both may be able to append information to the data log so as to create a richer body of data on which to judge compliance and efficacy for an assigned regime.

Figure 1:
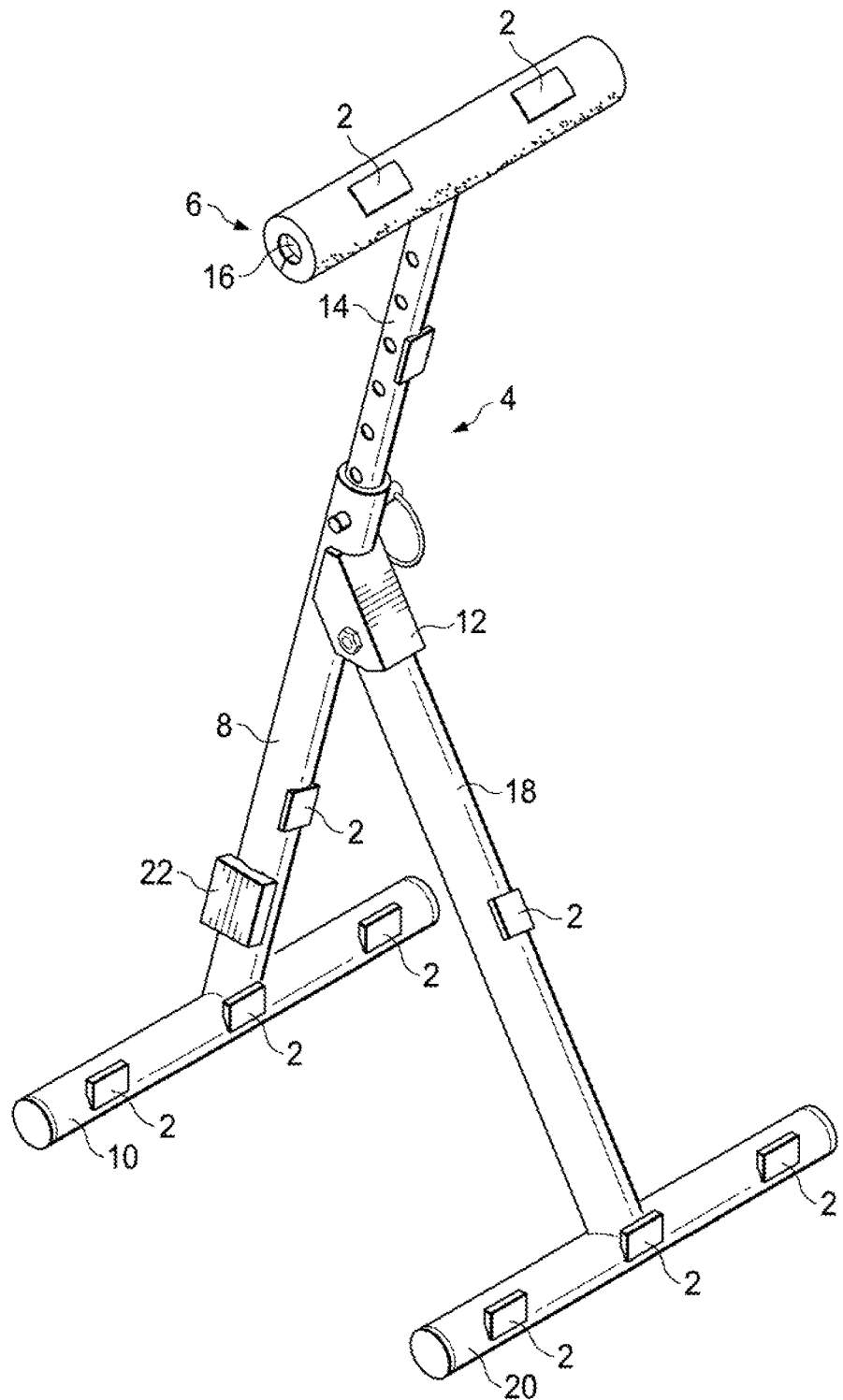
FIG. 1 illustrates an embodiment of a knee joint rehabilitation device.

As may be seen in the embodiment of FIG. 1, one or more sensors 2 may be attached at one or more locations to a physical therapy device 4 and/or peripheral components of the therapy device 4, such as a system of pads 6. Said sensors 2 may be bonded to the appropriate site by means of adhesives, stitching, or other mechanical means, or formed with the device as a portion thereof. Said sensors 2 may be permanently bonded or may be removably bonded. Removable or replaceable sensors 2 may be achieved by non-permanent adhesives, pockets to accept the sensor 2, mechanical devices such as clips or brackets. Permanently bonded sensors may utilize permanent adhesives, or be formed into the device 4 or pads 6. Stitching a sensor 2 to the device 4 or pads 6 may represent either permanent or replaceable bonding as determined by economics rather than physical design.

Said sensors 2 may comprise a single sensor or a network of sensors and maintain communication with other network devices through wired or wireless communication. These sensors 2 may operate to provide feedback about a therapy session. Such feedback may include but not be limited to: patient initiation and cessation of a physical therapy regime, start and stop times, how accurately the patient performs the prescribed actions, range of motion based on an array of sensors, positioning of the patient limbs on the device, positioning of the patient's body with respect to the device, orientation of the device with respect to support surfaces, and other data that may be used to analyze therapy compliance. Additionally, the sensors 2 may be arranged such that the pressure profile seen across the contact area of a limb may indicate which limb in particular is in contact with the device 4. For example, the medial region of the posterior face of a knee may generate greater pressure than the lateral region of said knee. This pressure gradient as compared to the intended geometric relation between the knee and device may then indicate whether the right or left knee is in contact with device 4.

Sensors 2 may be disposed on a physical therapy device 4 such as a knee flexion rehabilitation device 4, such as that disclosed in US Patent Publication No. 2016/0367427 (application Ser. No. 14/758,776), filed Jun. 30, 2015, and entitled Method and Apparatus for Knee Joint Flexibility Rehabilitation, the entire disclosure of which is incorporated herein by reference. Such a device is illustrated in FIG. 1. Such a knee joint flexibility rehabilitation apparatus 4 may comprise a tubular strut 8 having a first support foot 10 and a bracket 12 attached thereto, the tubular strut 8 forming a first aperture; a height-adjustment bar 14 translatably and rotatably disposed in the tubular strut 8, the height-adjustment bar 14 forming a plurality of second apertures extending through the cross-section of the height-adjustment bar 14; a support bar 16 fixed substantially perpendicularly to the height-adjustment bar 14, the support bar 16 having a pad 6 and being configured to receive a knee joint posterior; a support strut 18 pivotably connected to the bracket 12, the support strut 18 having a second support foot 20 attached thereto, the support strut 18 pivotable away from parallel the tubular strut 8 to form an acute angle thereto; and a pin removably disposed in one of the plurality of second apertures to fix the height-adjustment bar 14 against translation in one direction. The first foot 10 may be substantially perpendicular to the tubular strut 8, and the second foot 20 may be substantially perpendicular to the support strut 18. The support bar 16 may be padded. The bracket 12 may be configured to prevent travel of the support strut 18 away from the tubular strut 8 beyond a predetermined angle.

As illustrated in FIG. 1, sensors 2 may be disposed at the fulcrum bar 16 of a knee flexion device 4, along the height adjustment shaft 14, along the first support foot 10, the second support foot 20, any combination of the aforementioned locations, or any other location at which the patient may be in contact with the device 4. A data acquisition module 22 may be attached to said therapy device 4.

Figure 2:
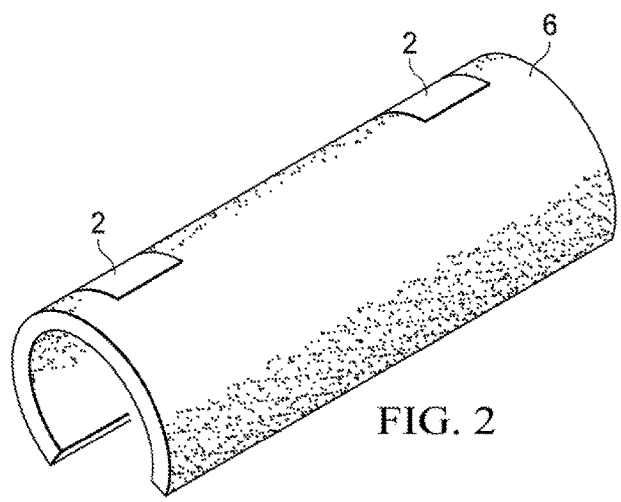
FIG. 2 illustrates an embodiment of a pad having a sensor.

As may be seen in the embodiment of FIG. 2, sensors 2 may also be disposed at ancillary components of the device such as on a pad 6, or a pad system comprising one or more pads such as that disclosed in International Application No. PCT/US2015/034019 (PCT Pub. No. WO 2016/195680), filed Jun. 3, 2015, and entitled Method and Apparatus for Variable Knee Flexion Support, the entire disclosure of which is incorporated herein by reference. Said pad or pads 6 may be used in conjunction with a physical therapy device 4 such as disclosed above or may allow many common items to be used as a therapy device 4. This may include chairs, bed rails, headboards, footboards, or any other apparatus of sufficient strength, geometry, and size. Such pads 6 may be deployed as single pad or as a set of pads.

Differing pad styles may require sensors 2 to disposed in differing locations on a pad. Said sensors 2 may be bonded on the surface of a pad 6, embedded into the pad's surface, or embedded deeper into the body of the pad 6 as allowed by the style of pad 6 and the nature of the sensor 2 type selected. Sensors may be provided in an array of sensors, such as in one or more rows of sensors. In other embodiments, a sensor may be removably disposed on or between pads. In such embodiments, a single sensor may be used with a system of multiple pads, and re-positioned after addition or removal of a pad.

Figure 3:
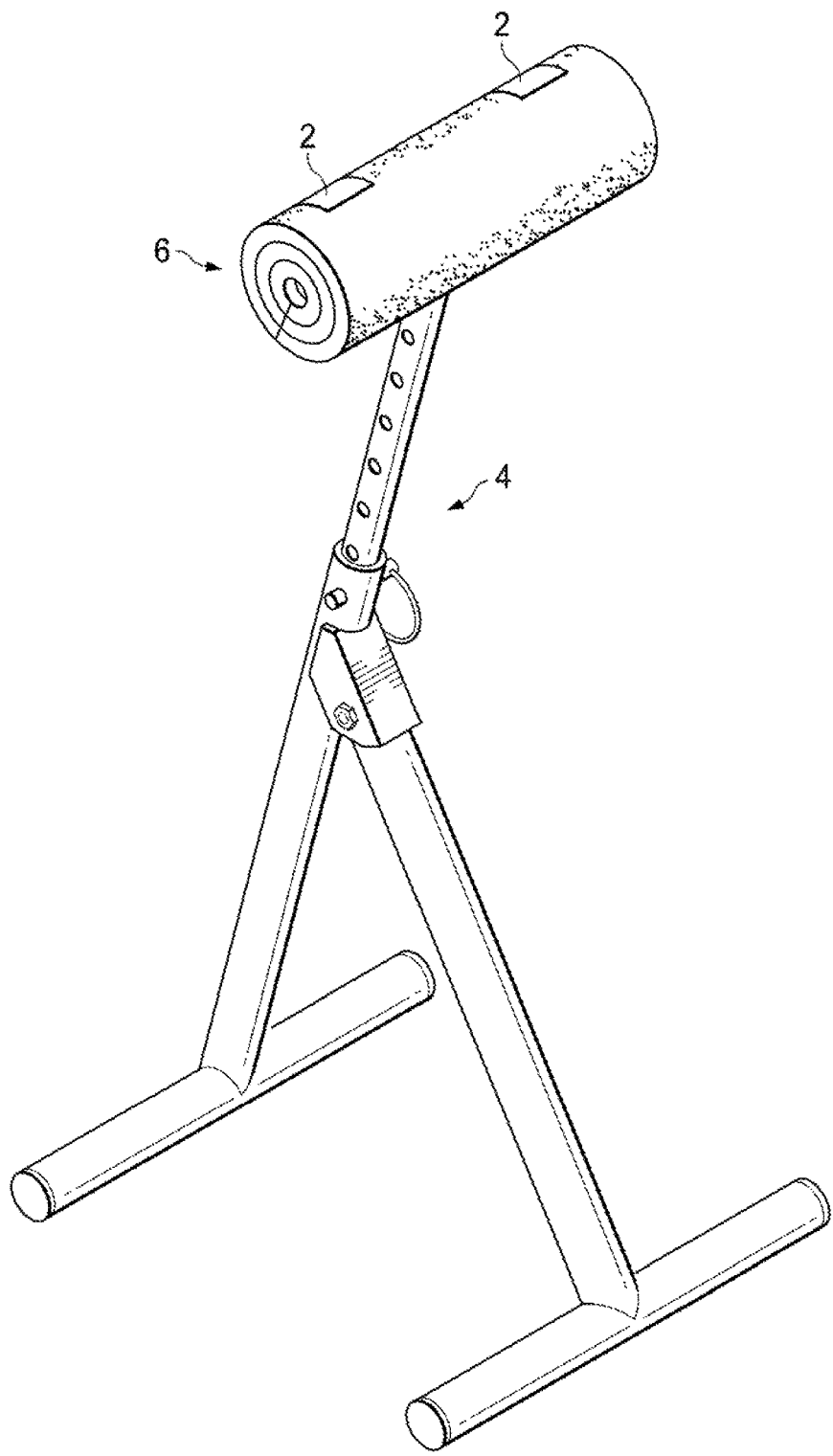
FIG. 3 illustrates an embodiment of a knee joint rehabilitation device having a system of pads thereon.

As may be seen in the embodiment of FIG. 3, a knee flexion rehabilitation device 4 may comprise a support bar 16 upon which a knee may rest. A knee support system 16 may utilize a pad system 6 of one or more pads may be deployed as described herein to permit incremental knee flexion. Sensors 2 may be disposed such that when the patient engages with the therapy device 4, contact is maintained between the patient and the sensors 2.

Figure 4:
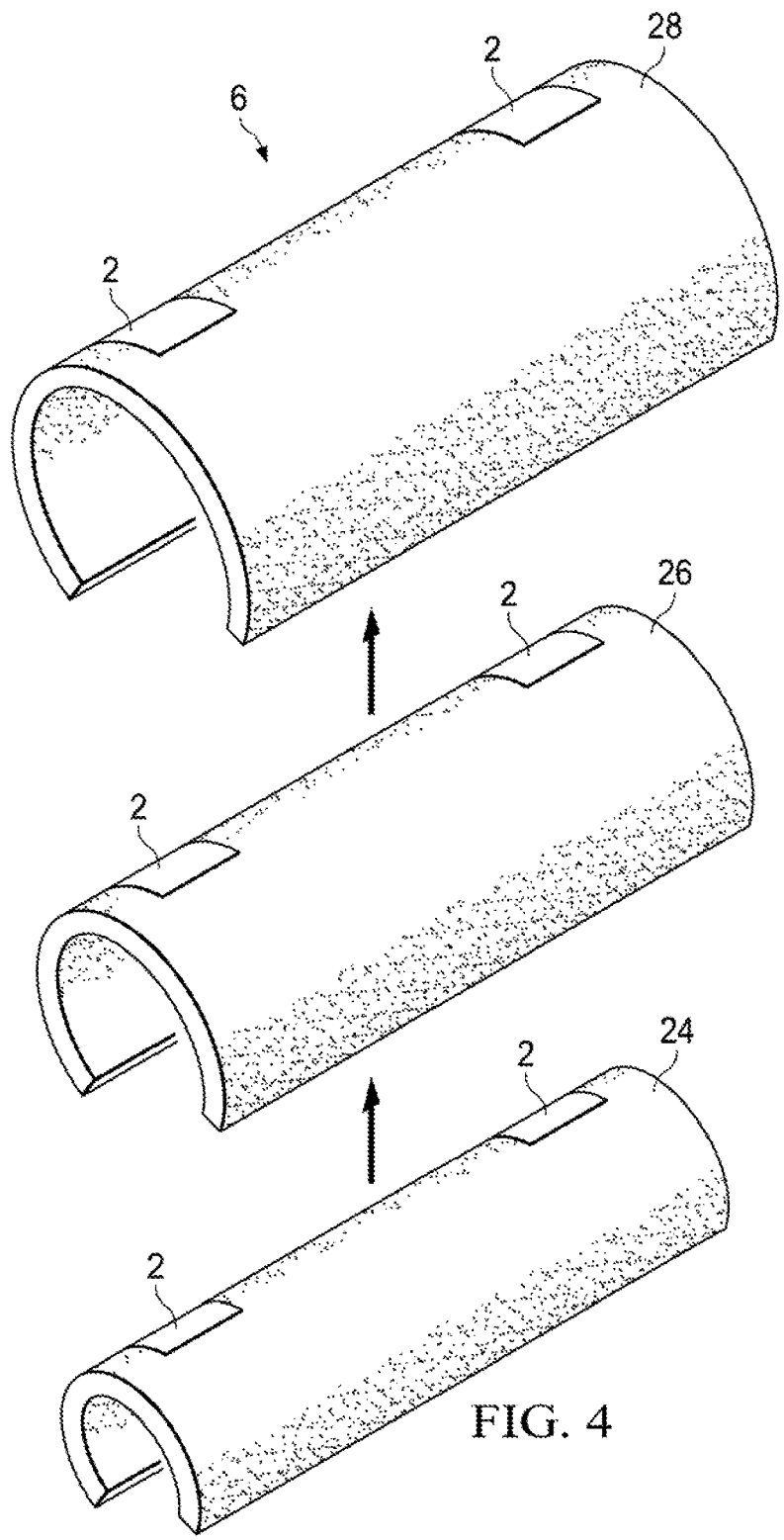
FIG. 4 illustrates an embodiment of a system of pads having sensors.

In one embodiment, as illustrated in FIG. 4, the pad system 6 may comprise a nested arrangement of pad layers. Each pad 6 may then have sensors 2 disposed so as to make contact with a patient during use of the therapy device 4. In such an embodiment, a base pad 24 may cover the support bar 16 as a first pad layer 24. A second pad layer 26 may cover the first pad layer 24, and a third pad layer 28 may cover the second pad layer 26.

A set of pads 6 may nest inside one another with sensors 2 disposed on or in the pad 24, 26, and 28. In the case of a set of nested pads, or where may otherwise be desired, the sensors 2 may be individually activated for monitoring from a central control station, such as therapist's tablet or workstation. Alternately, the sensors 2 may be so arranged as to sense the difference between an overlying pad 24, 26, and 28 versus an actual patient. Thus, sensors 2 on inner pads 24 and 26 may deactivate while only the sensors 2 on the outer pad 28 are active.

For example, this selectivity may be realized by the combination of a temperature sensor and force or pressure sensor working in combination. The temperature sensor may be utilized to differentiate between an overlying pad and a patient, while the force or pressure sensor is utilized to record the patient compliance data. The temperature and force or pressure sensors may be replaced with any combinations of sensor types that would allow the differentiation between human contact and contact from the nesting of an overlying pad. The sensor enhanced pad may also allow the system to be utilized with improvised therapy devices, such as a chair, bed rail, or any mechanism suitable for supporting the therapy regime.

Figure 5A:
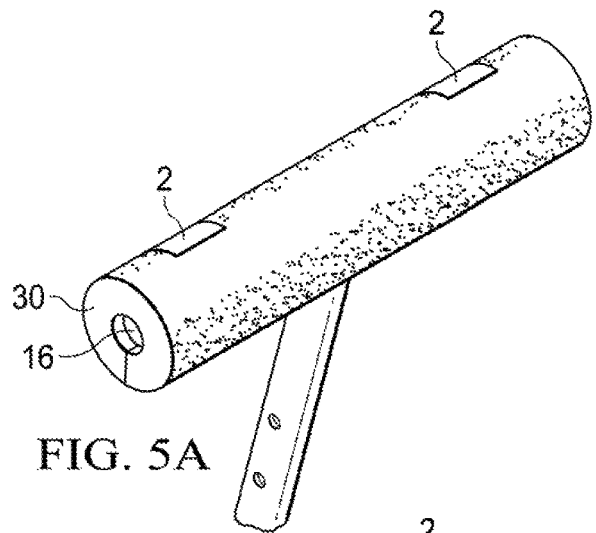
FIGS. 5A, 5B and 5C illustrates an embodiment of a system of pads having sensors.
Figure 5B:
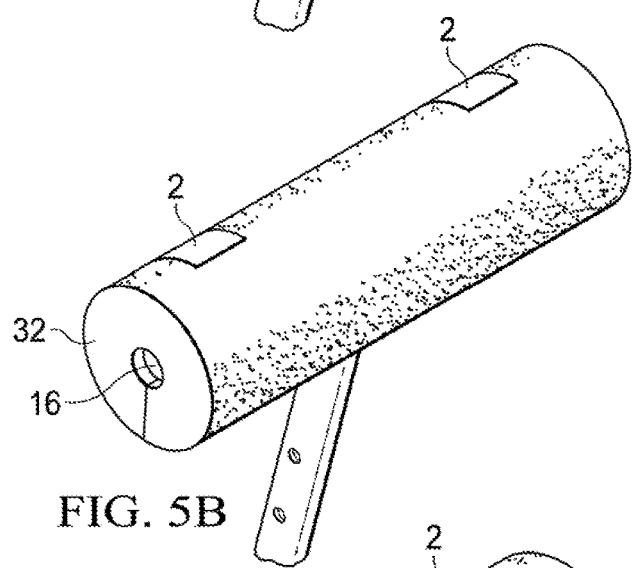
Figure 5C:
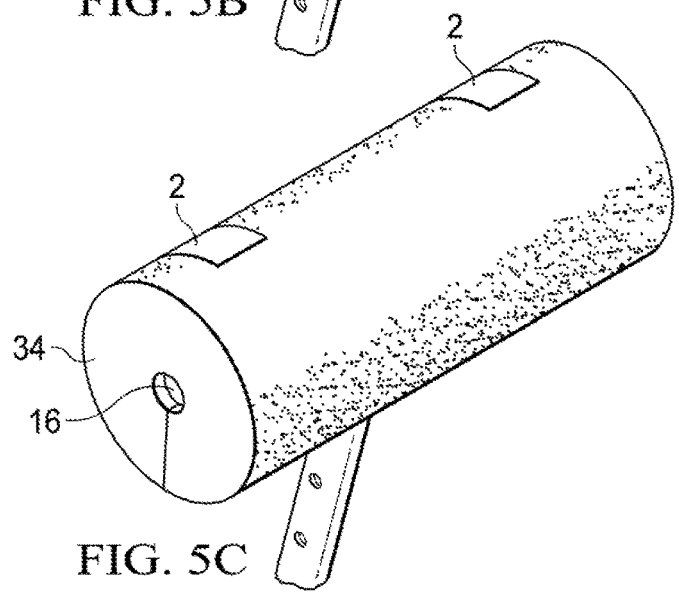

In the embodiment of FIGS. 5A-C, three pads 30, 32 and 34, may be used to provide for separate use on a support bar 16. Each of the three pads 30, 32, and 34 may have a different thickness, and each may thus provide a different effective diameter for the support bar 16. For example, instead of using first 24, second 26, and third pad layers 28 (FIG. 4) to effectively increase the diameter of the support bar 16, a single pad 30, 32, or 34 may be independently used to effectively achieve that same effective diameter provided by nesting pads. Similarly, a single pad 30, 32 or 34 may be used to achieve the same effective diameter provided by first and second pad layers 24 and 26, and a single pad may be used to achieve the same effective diameter provided by first pad layer 24. Thus, pad layers may be replaced by a small diameter pad 30, intermediate diameter pad 32, and large diameter pad 34. Such pads may have sensors 2 disposed at one or more locations on or in or between the pads.

Figure 6A:
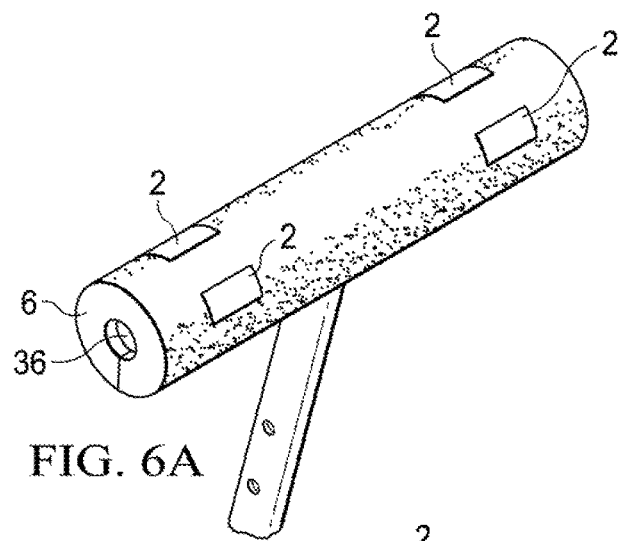
FIGS. 6A, 6B and 6C illustrate yet another embodiment of a system of pads having sensors.
Figure 6B:
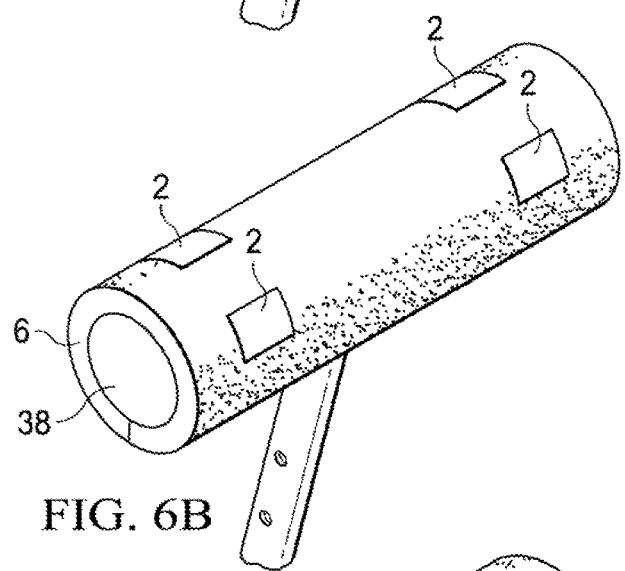
Figure 6C:
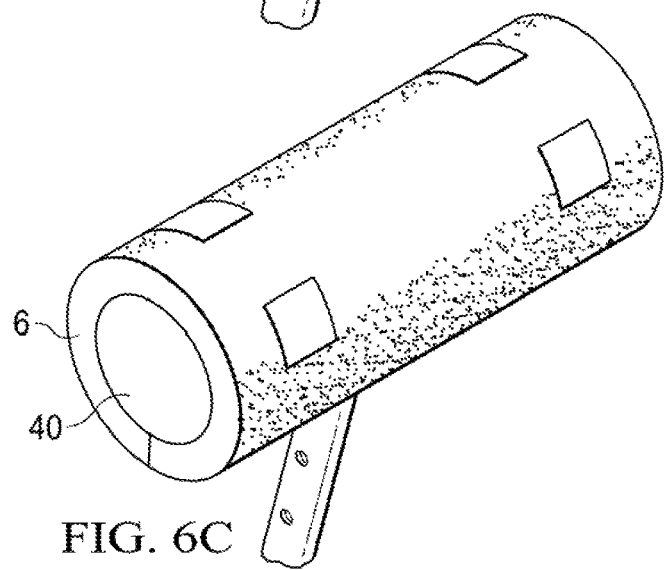

Alternately, as in FIGS. 6A-C, a set of pads 6 and a therapy device 4 may achieve a range of effective diameters by varying the diameter of the support bar 16 to which a pad 6 attaches, rather than the thickness of the pad 6. In such an embodiment, there may be a small diameter support bar 36, an intermediate diameter support bar 38, and a large diameter support bar 40, any of which may be covered with a pad 6. Such pads 6 may have one or more sensors 2 disposed at one or more locations on the pad 6. As noted above, a sensor may be removably placed on a pad or between pads or between a pad and support bar.

In some embodiments, the sensors may be located so as to achieve substantially continuous contact with a patient during a therapy session. A pad or system of one or more pads as described above may be used in connection with the device of FIG. 1, or may be used in connection with any suitably-configured support bar or surface, such as a rail, chair back, bed frame or bracket.

Figure 7A:
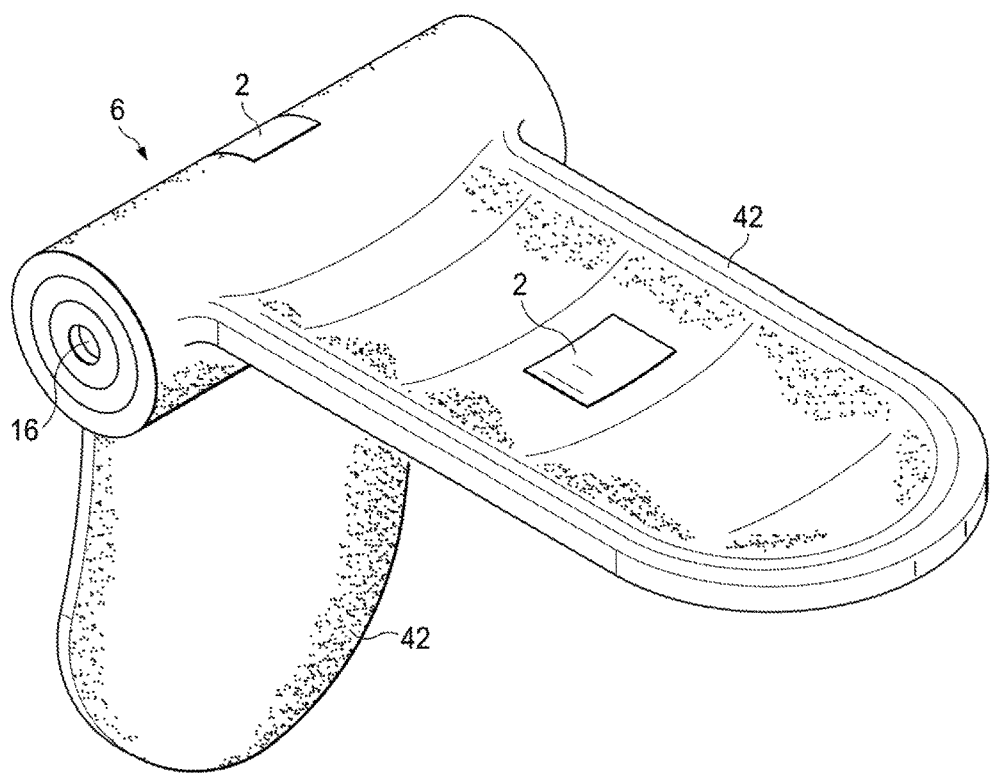
FIGS. 7A and 7B illustrate yet another embodiment of a system of pads having sensors.
Figure 7B:
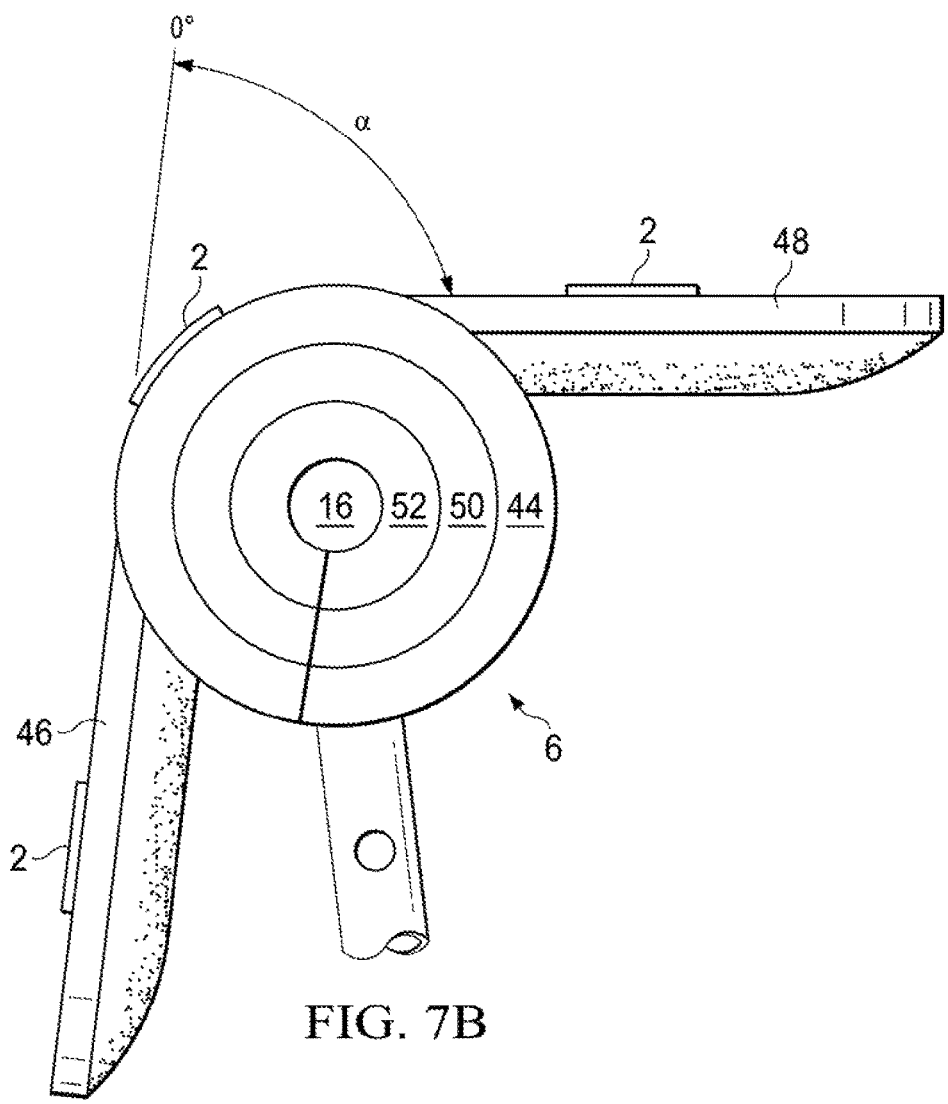

In other embodiments, as illustrated in FIG. 7, one or more of the pads 6 may be provided with one or more wings 42 against which the upper leg and/or lower leg may rest to further control range of motion. Each wing 42 may extend from a pad 6 at a tangent thereto. A single-wing 42 embodiment may be keyed to the support bar 16 so as to substantially restrict rotation of the wing 42 about the support bar 16. In the embodiment of FIG. 7A, the outer layer pad 44 may comprise a lower leg support wing 46 and a lower leg support wing 48 that may further support a patient's leg. When two wings are used, the lower leg support wing 48 may be positioned in a suitable angular range a from the lower leg support wing 46. The outer layer pad 44 may nest over an interior pad 50 which may in turn nest over an inner most pad 52. In such embodiments, sensors 2 may be disposed at the central body of the pad 6 and further sensors may be disposed along each wing 42 of the pad.

Figure 8:
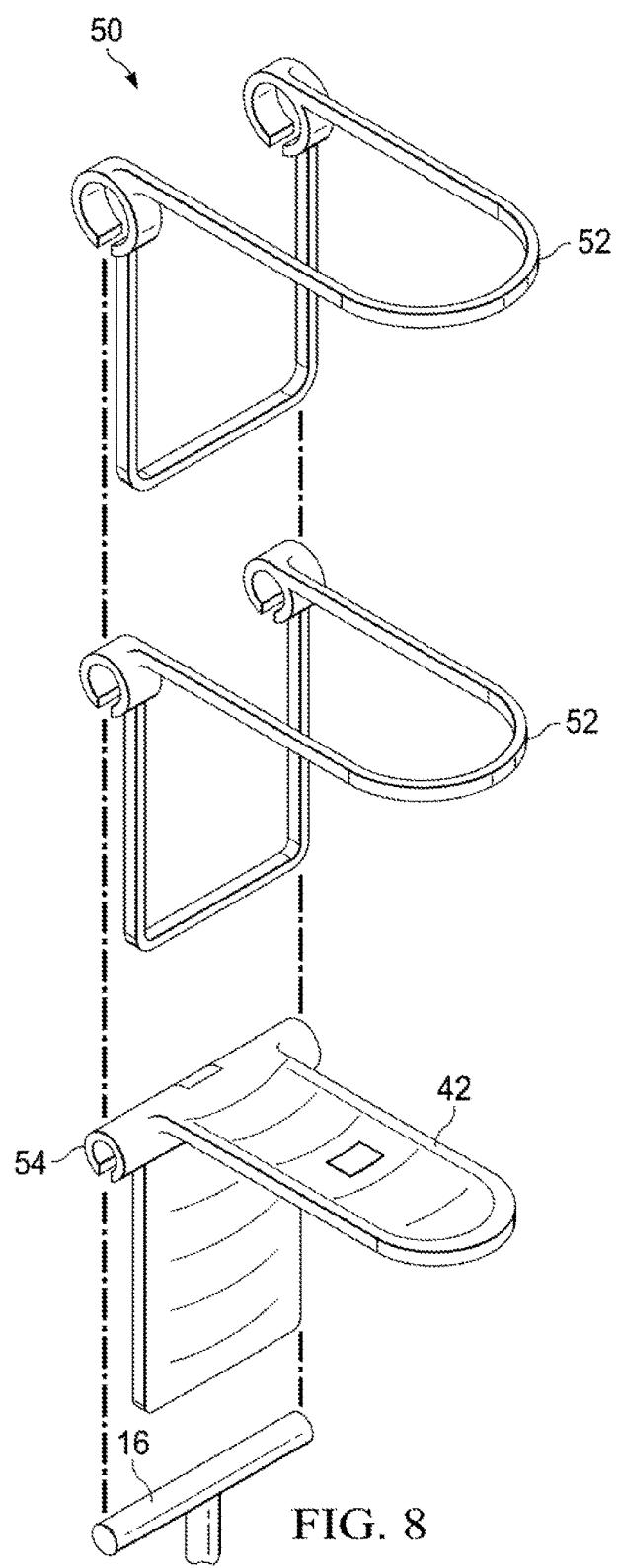
FIG. 8 illustrates yet another embodiment of a system of pads.

In some embodiments, such as those of FIG. 8, a system of layered pads 50 may provide nestable support wings 52. Of course, one or more wings 42 may also be provided on pads 50 configured for sequential mounting to a support bar 16. Such an embodiment may employ sensors 2 disposed at the wings 42 of each pad and at the central body 54 of any pad 52 having such.

Figure 9A:
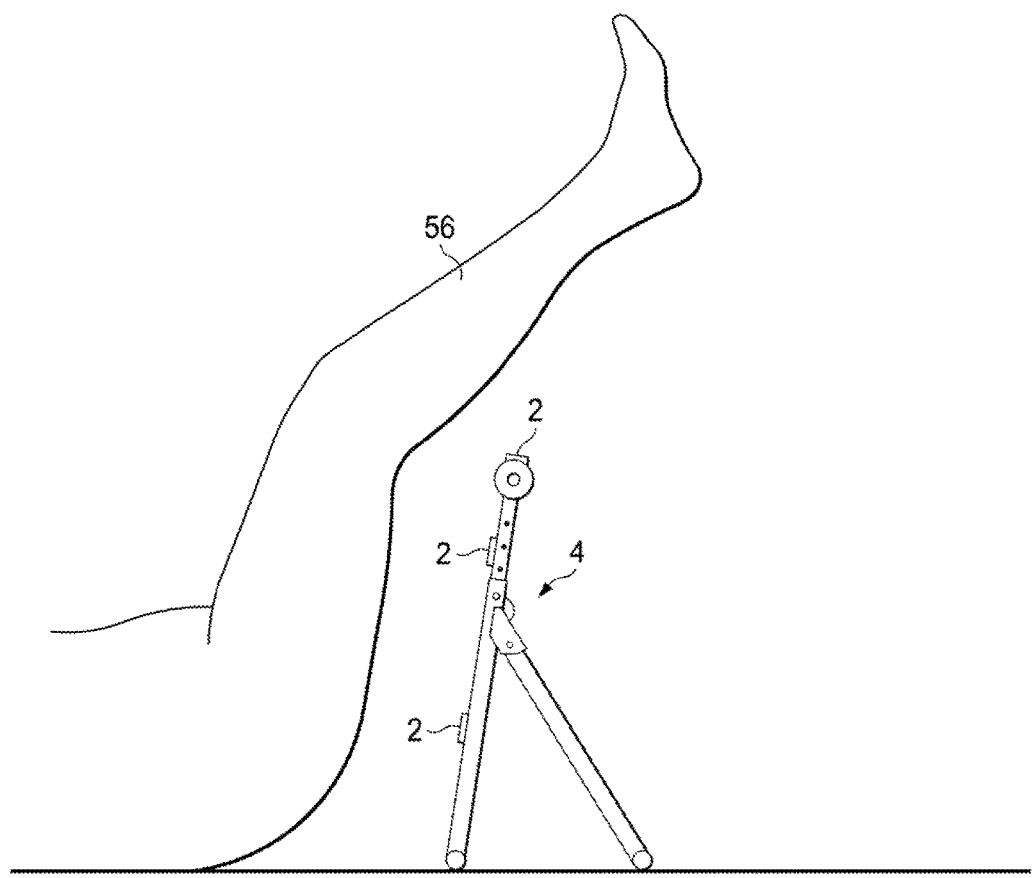
FIGS. 9A, 9B and 9C illustrate use of the embodiment of FIG. 1.
Figure 9B:
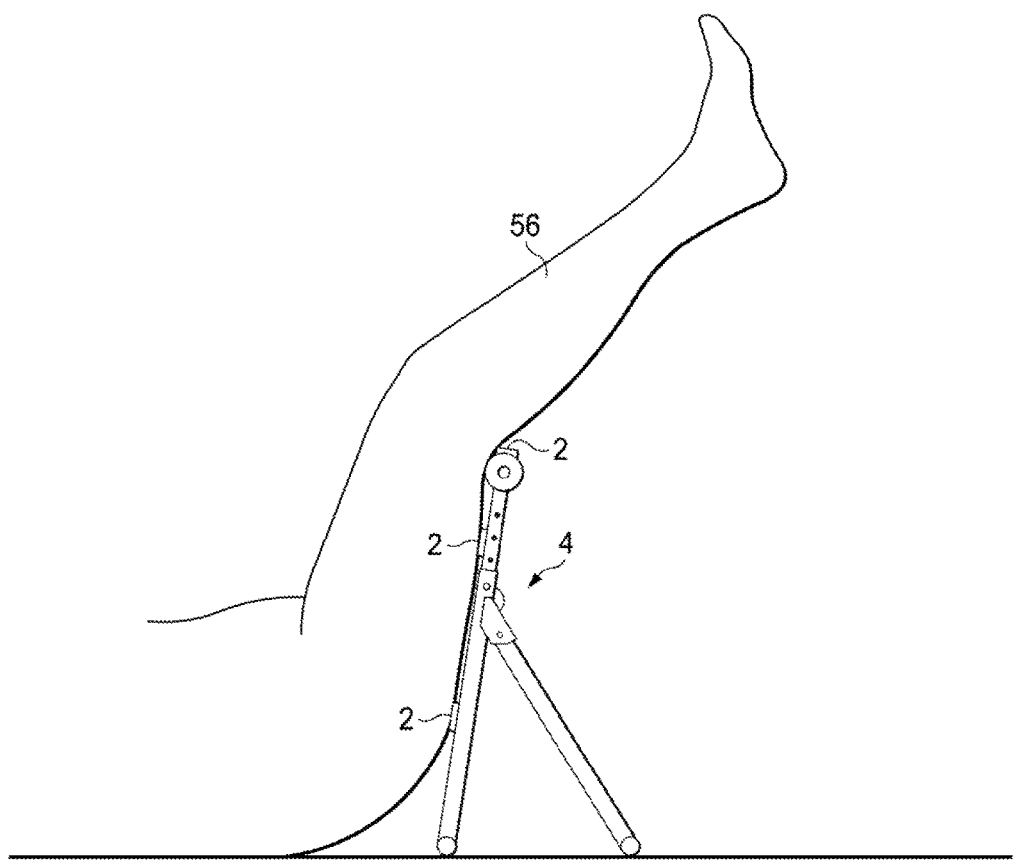
Figure 9C:
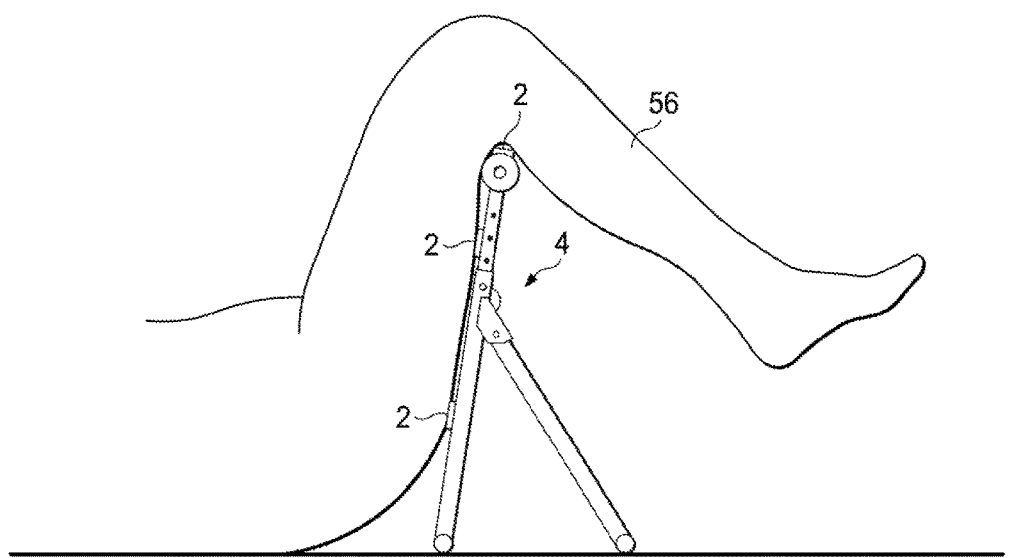

A patient 56 may make physical contact with a therapy device 4 before the patient 56 is prepared to begin a therapy session, as is illustrated in FIGS. 9A-C. In FIG. 9A, a patient 56 may be seen as preparing to engage the therapy device 4. In FIG. 9B, the patient 56 may make initial engagement with the therapy device for proper positioning of the therapy device with the patient body (here, the patient leg). In FIG. 9C, the patient 56 may establish proper positioning of the device with respect to the patient's body, and may be begin use of the device 4. A patient 56 may contact one or more of the sensors 2 of the system as the patient 56 brings their body into proper position. To alleviate false non-compliance data as a patient 56 makes these preparations and adjustments, the sensors may be pressure-sensitive, and in some embodiments a data log may not begin immediately recording at initial contact between patient 56 and sensors 2. In other embodiments, the sensor system may require that all or particular sensors 2 be in contact before initiating data recording. To further safeguard against premature data recording, the system may also require the patient or therapist to take an action to begin recording of data for the session. For example, a patient may have access to a smart device application and must engage a button to begin the session. Alternately, a therapist may have a control program that requires therapist interaction to begin recording data for the session. These human interactions may work in conjunction with any automatic data recording protocols in the system.

In some embodiments, sensor 2 may have a settling time, such as two seconds, between intermittent contact and a patient engaging with the therapy device. Upon patient 56 contact exceeding the settling time, the sensor network may begin to record the data log. Such a data log may include information on the length of time a patient 56 stays engaged in the regime, how much flexion in being generated at the knee, if the regime protocols are being met, and any other data which may be of use in establishing compliance and efficacy for a therapy session. This data may then be employed to analyze patient compliance with the established therapy regime.

Said sensors 2 may be temperature sensors, pressure sensors, force sensors, or a combination thereof. Specifically, the sensors 2 may be thermocouples, thermistors, piezoelectric mechanisms, strain gauges, and other common embodiments of the aforementioned general sensor types. These sensor types represent the most common sensors that may detect patient 56 contact with the therapy device 4, but other sensor types may be selected as desired.

Figure 10B:
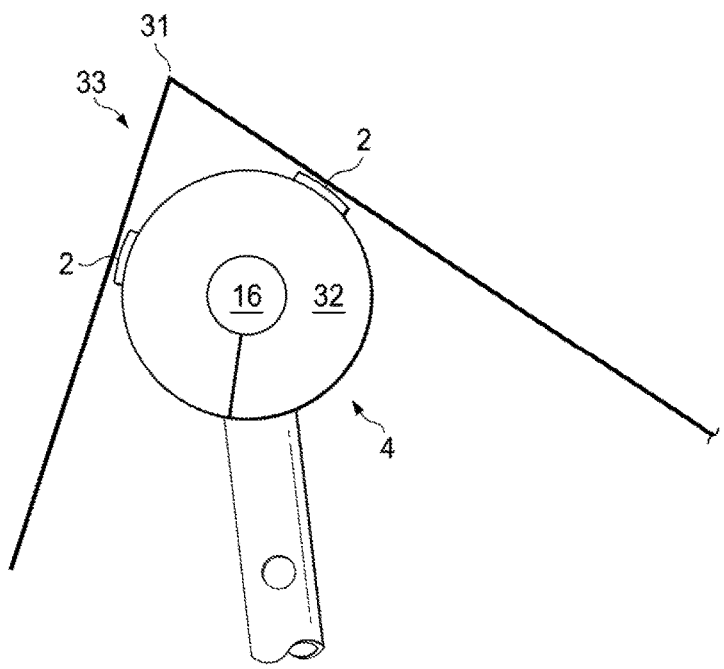
FIGS. 10A and 10B illustrate use of a system of pads having sensors.
Figure 10A:
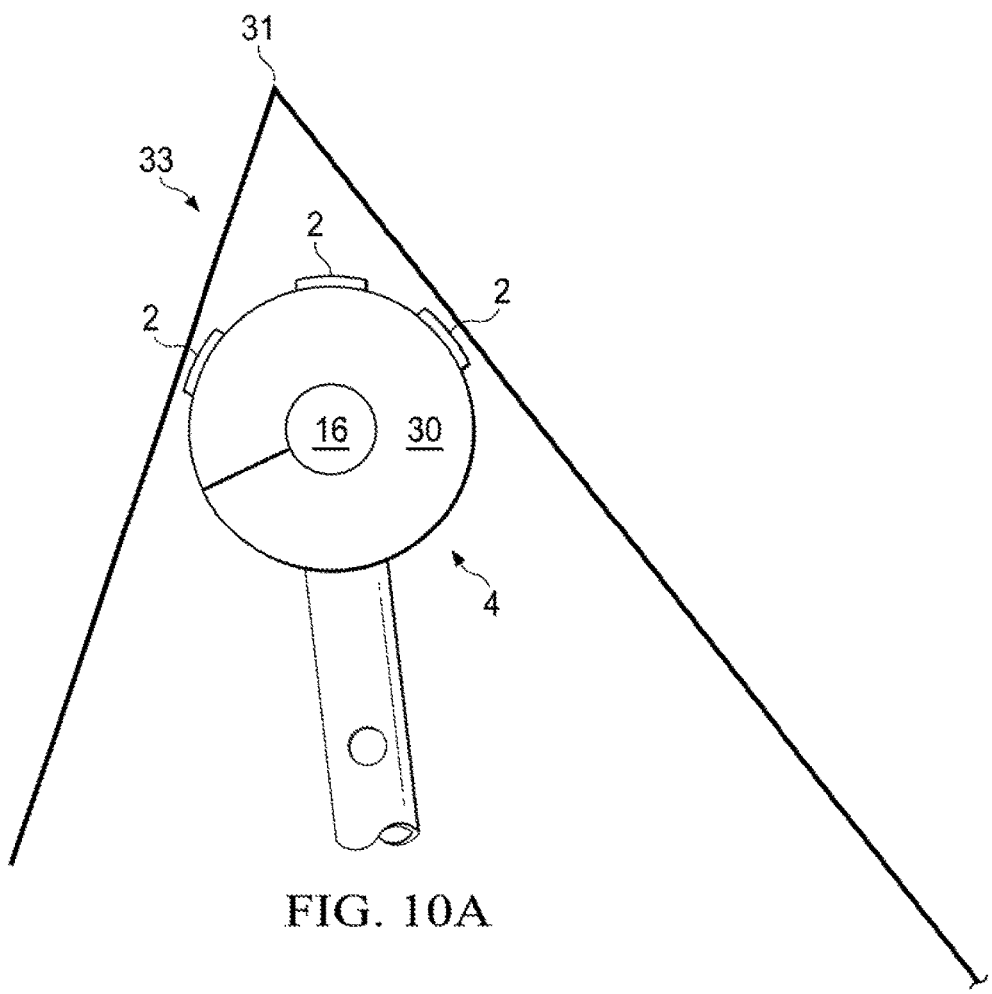

As illustrated in the embodiments of FIGS. 10A and 10B, a method of using the foregoing knee flexion rehabilitation device 4 may comprise removably mounting a first pad 30 to a support bar 16, the first pad 30 comprising a first outer diameter; positioning the support bar 16, having mounted the first pad 30, at the posterior of a knee joint 31 such that the limb 33 is in contact with the sensors 2 on the pad 30; moving the knee joint 31 through a first range of motion; removing the support bar 16 from the posterior of the knee joint 31; removing the first pad 30 from the support bar 16; removably mounting a second pad 32 to a support bar 16, the second pad 32 comprising a second outer diameter greater than the first outer diameter; positioning the support bar 16, having mounted the second pad 32, at the posterior of the knee joint 31; and moving the knee joint 31 through a second range of motion, and repeating such a process through all effective diameters as called for in the assigned therapy regime. One or more sensors 2 may detect placement of the limb (e.g., via pressure), and may send signals to a data logger for tracking patient compliance. Depending on the arrangement of the sensors 2, the data logger may calculate range of motion based on sensor data.

Figure 11A:
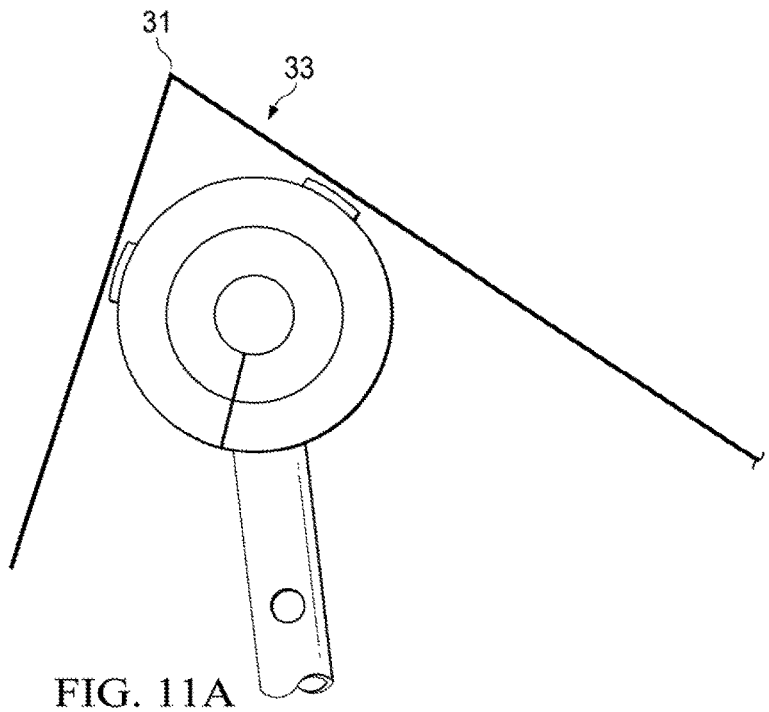
FIGS. 11A and 11B illustrate use of a system of pads having sensors.
Figure 11B:
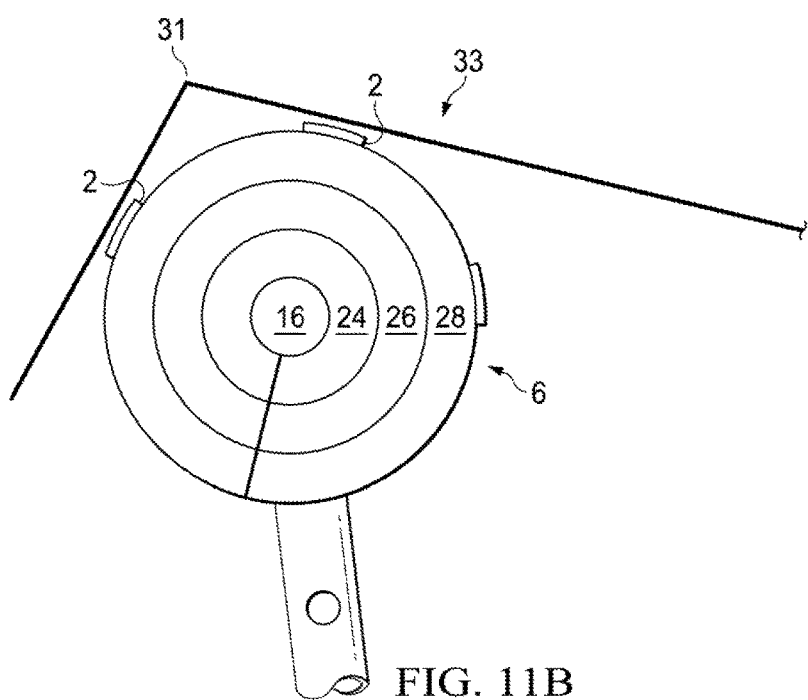

Alternately, as illustrated in the embodiments of FIGS. 11A and 11B, a method of using the foregoing knee flexion rehabilitation device 4 may comprise nestably and removably mounting a plurality of pads 6 to a support bar 16; positioning the support bar 16, having mounted the plurality of pads 6, at the posterior of a knee joint 31; moving the knee joint 31 through a first range of motion; removing the support bar 16 from the posterior of the knee joint 31; removing the outermost pad 28 of the plurality of pads 6 from the support bar 16; positioning the support bar 16, having the outermost pad removed 28, at the posterior of the knee joint 31; and moving the knee joint 31 through a second range of motion; repeating such a process through all effective diameters as called for in the therapy regime. During each stage of the therapy session, the limb 33 may remain in contact with the sensors 2 so as to monitor therapy compliance parameters. One or more sensors 2 may detect placement of the limb (e.g., via pressure), and may send signals to a data logger for tracking patient compliance. Depending on the arrangement of the sensors 2, the data logger may calculate range of motion based on sensor data.

As illustrated in the embodiment of FIGS. 10A-11B, sensors 2 may be so located that even as relative angles between the patient's limb 33 and the component (pad or support bar) on which the sensor 2 is disposed, the sensors 2 remain in contact with the patient. This may be accomplished by sensor geometry and placement. For example, a multitude of small sensors 2 may cover a significant portion of the contact surface and thus ensure continuous contact with the patient. Alternately, far fewer sensors 2 with large surface area may obtain the same results as the smaller sized sensors 2. Even further, a sensor 2 may be realized as a single entity of appropriate surface area.

The sensors 2 may maintain communication with other network devices through a data acquisition module 22 that attaches to the therapy device 4 being used. Such a module 22 may act as a data acquisition device for data collection, conditioning, and transmission. The module 22 may use wired or wireless protocols for communication with the sensors 2 and other devices in the network. The sensor data may then be made available to the physical therapy team member administering the regime through either a computer terminal or a smart device, such as a phone or tablet. In some embodiments, a data acquisition device may include a processor configured to receive and process data. Communication ports may allow for wired communication with a computer or server. In other embodiments, a transceiver may be provided in the data acquisition device for wireless communication with a computer, such as a desktop computer, a mobile device, and/or remote server. A computer storage medium may be used to store data.

Figure 12:
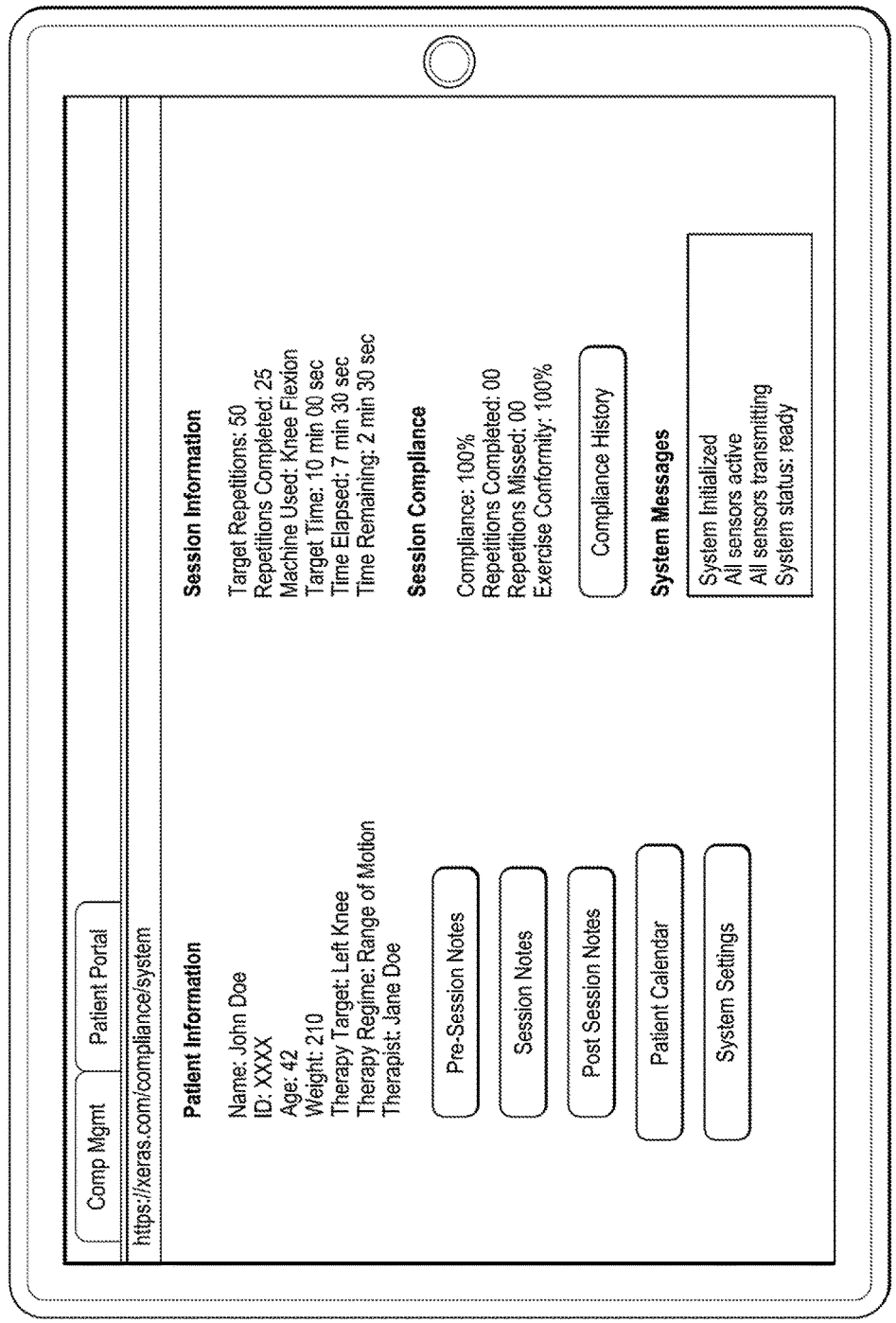
FIG. 12 illustrates an embodiment of a graphical user interface for a patient compliance tracking system.

An exemplary model of a web-based therapist interface may be seen in FIG. 12. Such an interface may include identifying information about the patient and the session to be performed. Such information may be entered by the administering therapist or may be automatically populated from other sources, such as orders from a physician, medical records, or other such entity. The interface may have links or buttons for the therapist to make notes on the session in question. Other links or buttons may allow the therapist to configure, initialize, calibrate, setup, customize, or preform other system related tasks. For example, the therapist may select input from a particular sensor network related to the therapy device to be used in the session. Also, the therapist may be able perform diagnostic functions prior to the initiation of the session, such as to ensure sensors are functioning properly. Said interface may also give on-screen feedback as to patient performance during the session and system functionality feedback. Other links and buttons on such an interface may include, but not be limited to, a patient calendar, compliance history, and other information relative to optimizing efficacy and compliance of a therapy session.

Figure 13:
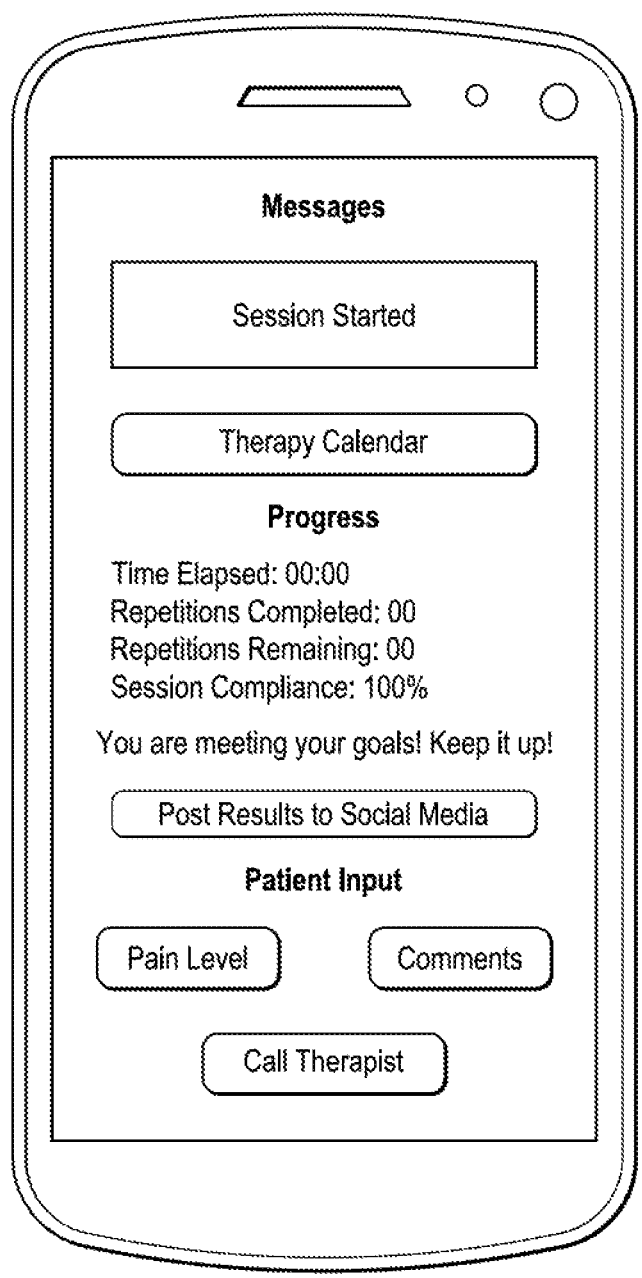
FIG. 13 illustrates an embodiment of a mobile device graphical user interface for a patient compliance tracking system.

The data may also be made available to the patient by means of a terminal or smart device, such as a phone or tablet, and thus allow compliance to be monitored by the patient, therapist, or both during a session in real time. A mobile application may be provided for installation on a mobile device. An application on a patient device may allow the patient to append information to the data timeline. An exemplary illustration of such an application may be seen in FIG. 13. Said information may be related to feedback such as pain levels, difficulty of performing the regime, or other pertinent data. Likewise, it may be possible for the therapist to make notes on the patient's performance and append this information to the sensor data timeline. Appending notes and input to the sensor data timeline may allow for a deeper understanding of the efficacy of the prescribed regime.

The system may be able to send reminders, alerts, and other pertinent information to a patient during the therapy session. The system may also maintain the ability to send such alerts and reminders to a patient prior or after a session. Such alerts and reminders may be in the form of phone notifications, emails, text messages, automated phone calls, or other electronic communication modalities. Reminders and alerts may remind patients of upcoming sessions and may also may include compliance related information during a session. Such information may tell the patient when to initiate the session, when to stop, and reminders to continue should the sensor network detect the patient has stopped before the prescribed terminal point. All such information may be appended to the data log timeline for inspection of a patient's compliance level.

Such an application may display messages to the patient, such as 'Session Started', 'Session Complete', 'Session Interrupted', and other communications to facilitate the execution of a session. Said application may have links and buttons to allow patient access and feedback pertaining to the therapy regime. These buttons and links may include a calendar, the ability to post results to social media, the ability to enter real time feedback as to pain level before, during, and after a session, comments to the therapist, and the ability to call for direct attention by a therapist. Said application may also give session feedback to the patient. For example, progress and goals for the session may be displayed on screen. Messages of encouragement and motivation also be delivered to the patient through the application.

Figure 14:
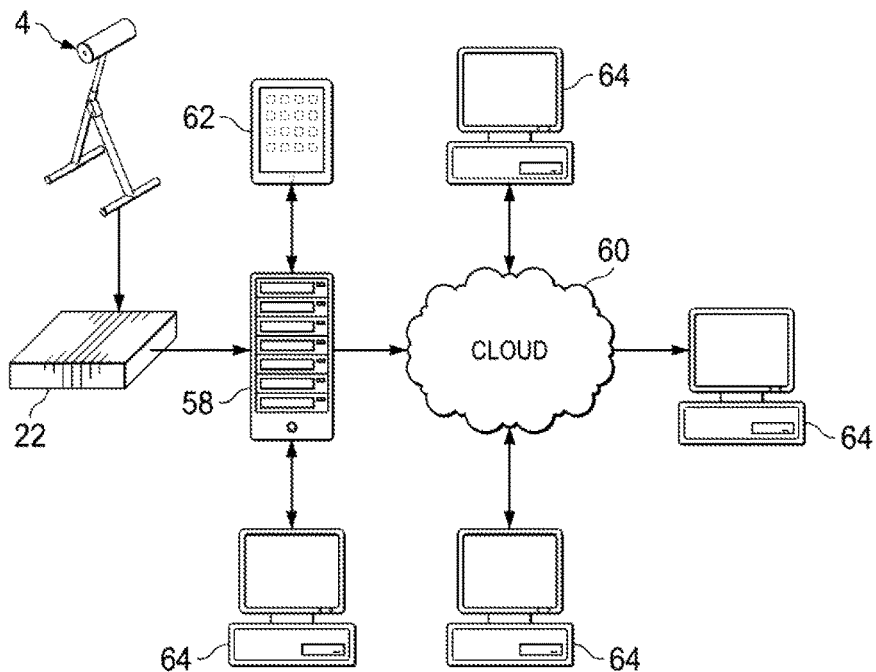
FIG. 14 illustrates an embodiment of patient compliance tracking system.
Figure 15:
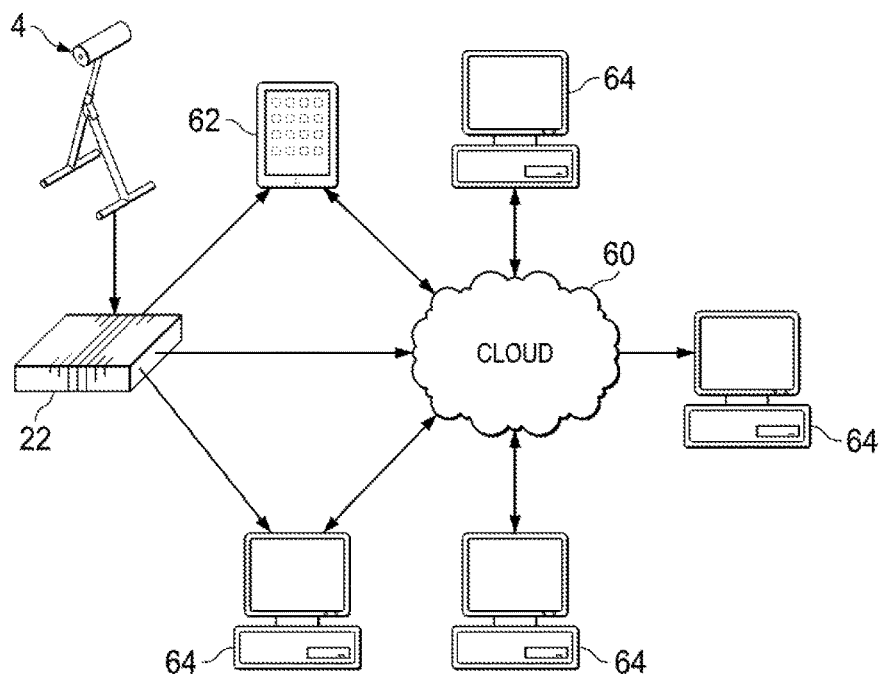
FIG. 15 illustrates another embodiment of patient compliance tracking system.
Figure 16:
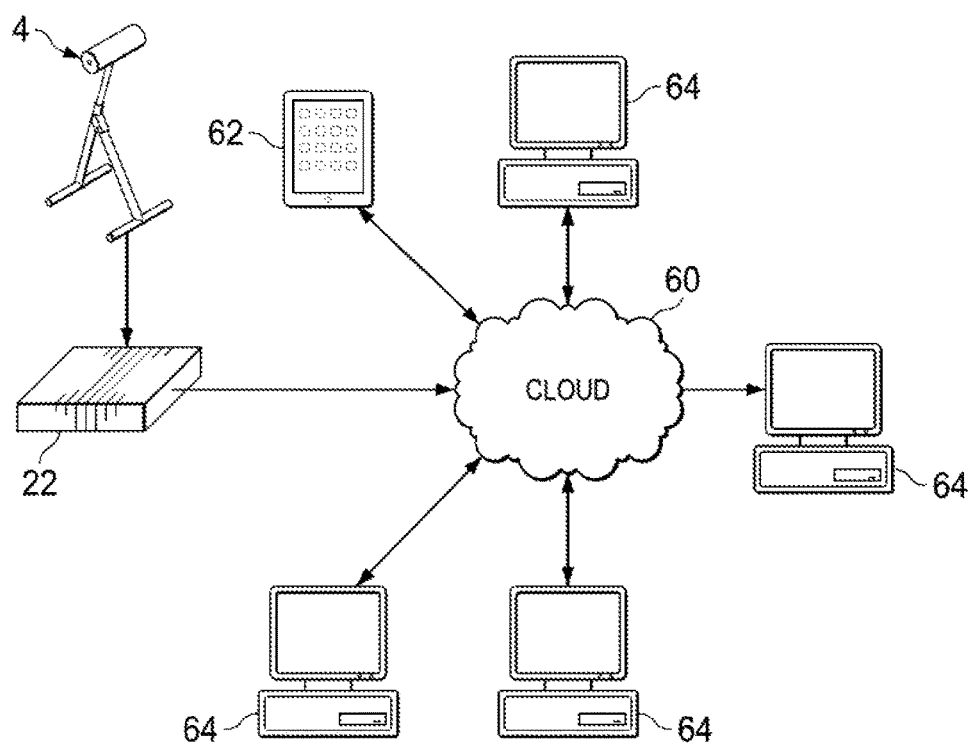
FIG. 16 illustrate yet another embodiment of patient compliance tracking system.

As illustrated in FIGS. 14-16, a system for detecting, recording, displaying and transmitting sensor data and compliance information may comprise a set of sensors (not shown) on a physical therapy device 4 that are networked to data acquisition (DAQ) devices 22 for processing, conditioning, storage, and utilization of data collected by said sensors. Such a network may comprise of said sensors, data acquisition modules 22 for data collection, processing, conditioning, and transmission, servers 58, cloud storage 60, and both mobile clients 62 and traditional clients 64. Alternately, a network may have the DAQ 22 communicate directly with client devices 62 and 64 and also the cloud 60 which negates the need for an internal server 58. In such an arrangement, patient and therapist client devices 62 and 64 may append to the sensor data log saved in the cloud 60. Yet again, a DAQ 22 may send all data solely to the cloud 60 and all client devices 62 and 64 may access the data from the cloud 60.

A location at which therapy is conducted may be equipped with a variety of computers, networks and related devices, such as servers, desktop computers, mobile communication devices, kiosks and monitors. Such equipment may be connected to form a computer system. Such a system may comprise client-server architecture. The system may comprise one or more servers in communication with one or more client devices via a communications network. In other embodiments, the system may comprise other types of network architecture, such as a peer-to-peer architecture, or any combination or hybrid thereof.

The servers may comprise one or more computers or programs that respond to commands or requests from one or more other computers or programs, or clients. The clients may comprise one or more computers or programs that issue commands or requests for service provided by one or more other computers or programs, or servers. The servers and clients may be located in or across one or more computers and/or geographic locations. Servers and/or clients may variously be or reside on, for example, mainframe computers, desktop computers, PDAs, smartphones, tablets, netbooks, portable computers, portable media players with network communication capabilities, cameras with network communication capabilities, wearable computers, point of sale devices, and the like.

As in FIG. 14, the data log may be recorded to an internal server for onsite physicians, researchers, and other approved entities to access. The data log may then be recorded to a cloud server for approved outside entities to access as needed. The information gathered on compliance may also be electronically or manually entered into the patient's medical records. The system may also maintain the ability to aggregate compliance data for multiple users to gather information pertaining to demographic analysis of patient compliance. Such aggregation may be realized by the direct transmittal of the data log to a database wherein which pertinent data fields may be populated directly from the data log. Alternately, said aggregation may be realized by gleaning data from medical records after pertinent information from the data log has been recorded to said records. These methods serve as two specific examples of how compliance information may be aggregated for research and other appropriate application. These examples are not meant to exclude any other commonly applied methods of obtaining aggregated data from a number of individual patient data logs.

In other embodiments, the DAQ may communicate with the cloud 60 and client devices 62 and 64 concurrently, as in FIG. 15. In such a configuration, the client devices 62 and 64 may be appending any information to the data log that the DAQ 22 is transmitting to the client devices 62 and 64. At the cloud 60 or at some other appropriate location in the system, a copy of the three data streams may be combined to create an appended version of the data log created by the DAQ 22.

Alternately, as in FIG. 16, data from the DAQ 22 may be sent directly to the cloud 60 so as to allow access by both internal and external approved entities without the need for an internal server at the therapy facility. Such a configuration may also allow for the sensor system to be used outside of clinical setting, such as home based therapy regimes. Data on the cloud may be stripped of personally identifying information or access to particular levels of personal information may be controlled by a tiered access-rights structure. This procedure may be implemented to ensure compliance with related laws as to the handling of patient medical and health data.

Although the disclosed subject matter and its advantages have been described in detail, it should be understood that various changes, substitutions and alterations can be made herein without departing from the disclosed subject matter as defined by the appended claims. Moreover, the scope of the claimed subject matter is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

We claim:

1. A knee joint flexibility rehabilitation apparatus comprising:
a tubular strut having a first support foot and a bracket attached thereto, the tubular strut forming a first aperture;
a height-adjustment bar translatably and rotatably disposed in the tubular strut, the height-adjustment bar forming a plurality of second apertures extending through a diameter of the height-adjustment bar;
a support bar fixed substantially perpendicularly to the height-adjustment bar, the support bar being configured to receive a knee joint posterior;
a support strut pivotably connected to the bracket, the support strut having a second support foot attached thereto, the support strut pivotable away from the tubular strut to form an acute angle thereto;
a pin removably disposed in one of the plurality of second apertures to fix the height-adjustment bar against translation in one direction; and
a sensor disposed and configured so as to sense reception of a knee joint posterior and generate a signal indicating such reception.

2. The apparatus of claim 1, the sensor being mounted to the support bar.

3. The apparatus of claim 1, the sensor being mounted to one of the support feet.

4. The apparatus of claim 1, wherein the support bar is padded and the sensor is mounted thereto.

5. The apparatus of claim 1, the sensor being mounted to the tubular strut.

6. A system for knee flexion support, the system comprising:
a knee support bar;
a plurality of pads configured to removably mount to the knee support bar, each pad having an outer diameter different from that of another of said plurality of pads; and
a sensor disposed on at least one of the plurality of pads, the sensor being configured so as to sense reception of a knee joint posterior and generate a signal indicating such reception.

7. The system of claim 6, wherein plurality of pads comprise a first pad configured to mount to the knee support bar and a second pad configured to nestably mount to the first pad, and the sensor is disposed between the first pad and the second pad.

8. The system of claim 6, wherein each of the plurality of pads is configured to allow a different range of motion for a knee joint.

9. The system of claim 6, wherein each of the plurality of pads comprises a color perceptibly different from that of another of said plurality of pads.

10. The system of claim 6, wherein each of the plurality of pads comprises a range-of-motion marking indicating the approximate range of knee joint motion allowed by said pad.

11. The system of claim 6, wherein the knee support bar is substantially rigid and substantially straight.

12. The system of claim 6, wherein the plurality of pads comprises a number of pads in a range of two to twenty pads.

13. The system of claim 6, wherein the plurality of pads comprises a number of pads in a range of two to twelve pads.

14. The system of claim 6, wherein the plurality of pads comprises three pads.

15. A knee joint flexibility rehabilitation apparatus comprising:
a tubular strut having a first support foot and a bracket attached thereto, the tubular strut forming a first aperture;
a height-adjustment bar translatably and rotatably disposed in the tubular strut, the height-adjustment bar forming a plurality of second apertures extending through a diameter of the height-adjustment bar;
a support bar fixed substantially perpendicularly to the height-adjustment bar, the support bar being configured to receive a knee joint posterior;
a plurality of pads configured to removably mount to the support bar, each pad having an outer diameter different from that of another of said plurality of pads;
a support strut pivotably connected to the bracket, the support strut having a second support foot attached thereto, the support strut pivotable away from the tubular strut to form an acute angle thereto;

a pin removably disposed in one of the plurality of second apertures to fix the height-adjustment bar against translation in one direction; and a sensor configured so as to sense reception of a knee joint posterior and generate a signal indicating such reception.

16. The system of claim 15, wherein plurality of pads comprise a first pad configured to mount to the support bar and a second pad configured to nestably mount to the first pad.

17. The system of claim 15, wherein each of the plurality of pads is configured to allow a different range of motion for a knee joint.

18. The system of claim 15, wherein the support bar is substantially rigid and substantially straight.

19. The system of claim 15, wherein the plurality of pads comprises a number of pads in a range of two to twelve pads.

20. The system of claim 15, wherein the plurality of pads comprises three pads.

\* \* \* \* \*